United States Patent
Lee et al.

(10) Patent No.: US 11,020,370 B2
(45) Date of Patent: Jun. 1, 2021

(54) PHARMACEUTICAL COMPOSITION FOR ORAL ADMINISTRATION COMPRISING HIGH CONCENTRATION TAXANE

(71) Applicant: DAE HWA PHARMA. CO., LTD., Gangwon-do (KR)

(72) Inventors: In-Hyun Lee, Gwangju (KR); Min-Hee Son, Uiwang-si (KR); Yeong-Taek Park, Ansan-si (KR); Han-Koo Lee, Seoul (KR)

(73) Assignee: DAE HWA PHARMA. CO., LTD., Gangwon-do (KR)

( * ) Notice: Subject to any disclaimer, the term of this patent is extended or adjusted under 35 U.S.C. 154(b) by 64 days.

(21) Appl. No.: 15/748,691

(22) PCT Filed: Apr. 6, 2016

(86) PCT No.: PCT/KR2016/003552
§ 371 (c)(1),
(2) Date: Jan. 30, 2018

(87) PCT Pub. No.: WO2017/018634
PCT Pub. Date: Feb. 2, 2017

(65) Prior Publication Data
US 2019/0000792 A1    Jan. 3, 2019

(30) Foreign Application Priority Data

Jul. 30, 2015 (KR) .................. 10-2015-0108002

(51) Int. Cl.
| | | |
|---|---|---|
| *A61K 31/337* | (2006.01) | |
| *A61K 31/215* | (2006.01) | |
| *A61K 31/22* | (2006.01) | |
| *A61K 47/44* | (2017.01) | |
| *A61K 9/48* | (2006.01) | |
| *A61K 47/14* | (2017.01) | |
| *A61K 47/26* | (2006.01) | |
| *A61K 47/34* | (2017.01) | |
| *A61P 35/02* | (2006.01) | |

(52) U.S. Cl.
CPC .............. *A61K 31/337* (2013.01); *A61K 9/48* (2013.01); *A61K 31/215* (2013.01); *A61K 31/22* (2013.01); *A61K 47/14* (2013.01); *A61K 47/26* (2013.01); *A61K 47/34* (2013.01); *A61K 47/44* (2013.01); *A61P 35/02* (2018.01)

(58) Field of Classification Search
CPC ..................................................... A16K 31/337
USPC ....................................................... 514/449
See application file for complete search history.

(56) References Cited

U.S. PATENT DOCUMENTS

| | | | |
|---|---|---|---|
| 6,348,491 | B1 | 2/2002 | Chu et al. |
| 8,075,917 | B2 | 12/2011 | Chung et al. |
| 2004/0092428 | A1 | 5/2004 | Chen et al. |
| 2006/0104999 | A1 | 5/2006 | Chung et al. |
| 2010/0310661 | A1 | 12/2010 | Chen et al. |

FOREIGN PATENT DOCUMENTS

| | | | |
|---|---|---|---|
| KR | 10-2007-0058776 | A | 6/2007 |
| KR | 20070058776 | A * | 6/2007 |
| WO | WO2013045357 | A1 * | 3/2006 |

OTHER PUBLICATIONS

Translation of KR20070058776A (Year: 2007).*
Ahmad et al., "Solid-Nanoemulsion Preconcentrate for Oral Delivery of Paclitaxel: Formulation Design, Biodistribution, and γ Scintigraphy Imaging", BioMed Research International, 2014, Article ID 984756, 1-12 pages, (2014).
Huizing et al., "Taxanes: A New Class of Antitumor Agents", Cancer Inv., 1995, 13: 381-404.
Eiseman et al, Second NCI Workshop on Taxol and Taxus (Sep. 1992), Suffness (ed.) et al, TaxolTM Science and Applications, CRC Press (1995).
Walle et al, "Taxol Transport by Human Intestinal Epithelial CACO-2 Cells", Drug Metabo. Disp. 26(4): 343-346 (1998).
The extended European Search Report for corresponding EP Application No. 16830668.6, dated Feb. 20, 2019, 4 pages.

* cited by examiner

*Primary Examiner* — Taina D Matos Negron
(74) *Attorney, Agent, or Firm* — Vorys, Sater, Seymour & Pease LLP; Mih Suhn Koh

(57) ABSTRACT

The present invention provides a pharmaceutical composition for oral administration, comprising (a) 4 to 40% by weight of a taxane, (b) 10 to 30% by weight of a medium chain triglyceride, (c) 30 to 70% by weight of monooleoyl glycerol, (d) 5 to 30% by weight of a surfactant, and (e) 10 to 30% by weight of polyoxyl glyceryl fatty acid ester and a process for preparing the same.

3 Claims, 1 Drawing Sheet

PHARMACEUTICAL COMPOSITION FOR ORAL ADMINISTRATION COMPRISING HIGH CONCENTRATION TAXANE

TECHNICAL FIELD

The present invention relates to a pharmaceutical composition for oral administration comprising a taxane in a high concentration. More specifically, the present invention relates to a taxane-containing pharmaceutical composition for oral administration comprising polyoxyl glyceryl fatty acid ester.

BACKGROUND ART

Taxanes, which are an anticancer agent showing their anti-proliferative effect by acting on the organization of the microtubules in the cellular cytoskeletal system (Huizing M. T. et al., Cancer Inv., 1995, 13: 381-404), are known to exhibit excellent cytotoxicity against various kinds of cancers such as ovarian cancer, breast cancer, esophagus cancer, melanoma and leukemia. Parenteral dosage forms of paclitaxel and docetaxel are commercially available under the trademarks Taxol™ and Taxotere™, respectively. Since a taxane is known to have very low water solubility, the currently available paclitaxel-containing formulation, e.g., Taxol™, has been formulated into the form of emulsion preconcentrate, which is diluted before using for injection. However, in order to overcome the problems related to patient compliance due to the use of the injection form, stability of the formulation, and safety to the human body, etc., researches on the formulations for oral administration are being carried out.

Meanwhile, it has been reported that the oral administration of a taxane such as paclitaxel exhibits very low oral bioavailability due to the action of an outwardly directed efflux pump (Walle et al, Drug Metabo. Disp. 26(4): 343-346 (1998)). It has been also reported that the orally administered paclitaxel is very poorly absorbed (less than 1%) (Eiseman et al, Second NCI Workshop on Taxol and Taxus (sept. 1992), Suffness (ed.) et al, Taxol™ Science and Applications, CRC Press (1995)). As an attempt to improve such a low oral bioavailability, Korean Patent Publication No. 10-2004-0009015 has disclosed a solubilized taxane-containing composition for oral administration, which is formulated by using a medium chain triglyceride such as triacetin, a monoglyceride such as monoolein, and a surfactant such as Tween. Said composition is a solubilized taxane-containing composition for oral administration, whose bioavailability is increased through high mucoadhesive property in the intestine by the monoglyceride such as monoolein. And also, Korean Patent Publication No. 10-2007-0058776 has disclosed an improved process for preparing the solubilized taxane-containing composition for oral administration, the process comprising dissolving paclitaxel, along with a medium chain triglyceride, a monoglyceride, and surfactant, in an organic solvent.

Solid formulations such as soft capsules have advantages in terms of the ease of use, compared to the lipid solution form. Considering the patient's compliance, it is necessary to control the size of the soft capsules to an appropriate size. Therefore, in order to prepare a soft capsule containing the therapeutically effective amount of a taxane, it is required to prepare a lipid solution containing the taxane in a high concentration. However, when a taxane is contained in a high concentration (for example, 4% by weight or more) according to conventional formulation methods (e.g., Korean Patent Publication Nos, 10-2004-0009015 and 10-2007-0058776), the taxane is precipitated from the lipid solution and thus the completely solubilized lipid solution cannot be obtained, thereby leading to the problem of decreased bioavailability.

DISCLOSURE

Technical Problem

The present inventors carried out various researches in order to develop a pharmaceutical composition for oral administration, for example in a capsule form, comprising a taxane in a high concentration. The present inventors have found that, when formulation processes are performed by adding polyoxyl glyceryl fatty acid ester additionally to the conventional paclitaxel-containing compositions (e.g., the compositions prepared according to Korean Patent Publication Nos. 10-2004-0009015 and 10-2007-0058776), a clear solution containing a taxane in a high concentration can be obtained, thereby being able to be formulated into a capsule form such as a soft capsule without the formation of a precipitate.

Therefore, it is an object of the present invention to provide a taxane-containing pharmaceutical composition for oral administration which is formulated by using polyoxyl glyceryl fatty acid ester as a solubilizing agent.

And also, it is another object of the present invention to provide a process for preparing the pharmaceutical composition for oral administration.

Technical Solution

In accordance with an aspect of the present invention, there is provided a pharmaceutical composition for oral administration, comprising (a) 4 to 40% by weight of a taxane, (b) 10 to 30% by weight of a medium chain triglyceride, (c) 30 to 70% by weight of monooleoyl glycerol, (d) 5 to 30% by weight of a surfactant, and (e) 10 to 30% by weight of polyoxyl glyceryl fatty acid ester.

In an embodiment, the polyoxyl glyceryl fatty acid ester may be one or more selected from the group consisting of caprylocaproyl polyoxyl glyceride, lauroyl polyoxyl glyceride, and stearoyl polyoxyl glyceride.

In accordance with another aspect of the present invention, there is provided a process for preparing a pharmaceutical composition for oral administration, comprising (i) dissolving 4 to 40% by weight of a taxane and 10 to 30% by weight of polyoxyl glyceryl fatty acid ester in an organic solvent, (ii) removing the organic solvent from the solution obtained in Step (i), followed by mixing 10 to 30% by weight of a medium chain triglyceride, 30 to 70% by weight of monooleoyl glycerol, and 5 to 30% by weight of a surfactant therewith to form a solution, and (iii) optionally, filling the solution obtained in Step (ii) in a capsule.

In accordance with still another aspect of the present invention, there is provided a process for preparing a pharmaceutical composition for oral administration, comprising (i') dissolving 4 to 40% by weight of a taxane, 10 to 30% by weight of a medium chain triglyceride, 30 to 70% by weight of monooleoyl glycerol, 5 to 30% by weight of a surfactant, and 10 to 30% by weight of polyoxyl glyceryl fatty acid ester in an organic solvent, (ii') removing the organic solvent from the solution obtained in Step (i'), and (iii') optionally, filling the solution obtained in Step (ii') in a capsule.

Advantageous Effects

It has been found by the present invention that, when formulation processes are performed by adding polyoxyl glyceryl fatty acid ester to a lipid solution comprising a taxane, a medium chain triglyceride, monooleoyl glycerol, and a surfactant, a clear solution containing a taxane in a high concentration can be obtained, thereby being able to be formulated into a capsule form such as a soft capsule without the formation of a precipitate. Therefore, the pharmaceutical composition for oral administration according to the present invention makes it possible to formulate into solid formulations such as soft capsules.

BEST MODE

Figure 1:
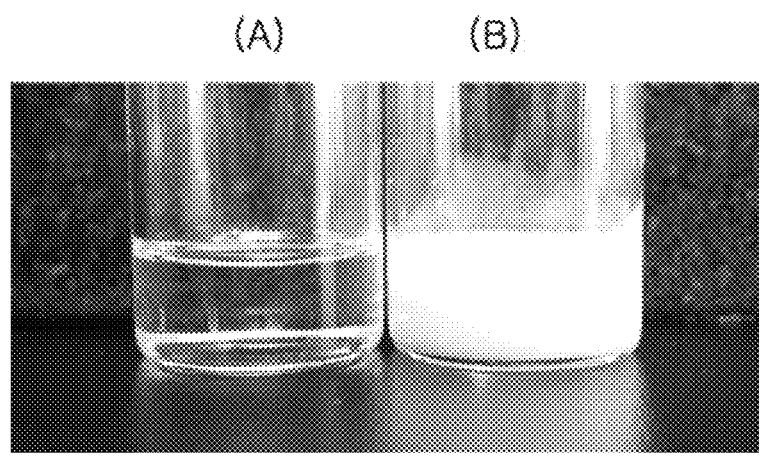
FIG. 1 represents the appearances of the docetaxel-containing lipid solutions prepared in Example 1 and Comparative Example 1. A: the docetaxel-containing lipid solution prepared in Example 1, B: the docetaxel-containing lipid solution prepared in Comparative Example 1.

The present invention provides a pharmaceutical composition for oral administration, comprising (a) 4 to 40% by weight of a taxane, (b) 10 to 30% by weight of a medium chain triglyceride, (c) 30 to 70% by weight of monooleoyl glycerol, (d) 5 to 30% by weight of a surfactant, and (e) 10 to 30% by weight of polyoxyl glyceryl fatty acid ester.

It has been found by the present invention that, when formulation processes are performed by adding polyoxyl glyceryl fatty acid ester to a lipid solution comprising a taxane, a medium chain triglyceride, monooleoyl glycerol, and a surfactant, a clear solution containing a taxane in a high concentration can be obtained, thereby being able to be formulated into a capsule form such as a soft capsule without the formation of a precipitate.

The polyoxyl glyceryl fatty acid ester may be one or more selected from the group consisting of caprylocaproyl polyoxyl glyceride, lauroyl polyoxyl glyceride, and stearoyl polyoxyl glyceride. Preferably, the polyoxyl glyceryl fatty acid ester may be one or more selected from the group consisting of caprylocaproyl polyoxyl-32 glyceride (e.g., LABRASOL™, etc.), lauroyl polyoxyl-32 glyceride (e.g., Gelucire™ 44/14, etc.), and stearoyl polyoxyl-32 glyceride (e.g., Gelucire™ 50/13, etc.).

The taxane includes one or more selected from the group consisting of paclitaxel, docetaxel, 7-epipaditaxel, t-acetylpaclitaxel, 10-desacetylpaclitaxel, 10-desacetyl-7-epipaclitaxel, 7-xylosyl pad itaxel, 10-desacetyl-7-glutarylpaclitaxel, 7-N,N-dimethylglycylpaclitaxel, 7-L-alanylpaclitaxel, and so on. For example, the taxane may be paclitaxel and/or docetaxel.

The medium chain triglyceride means a substance in which three molecules of saturated or unsaturated $C_2$-$C_{20}$ fatty acids and one molecule of glycerol are linked by ester bond. For example, the medium chain triglyceride includes triacetin, tripropionin, tributyrin, trivalerin, tricaproin, tricaprylin (e.g., Captex™ 8000 etc.), tricaprin, triheptanoin, trinonanoin, triundecanoin, trilaurin, tritridecanoin, trimyristin, tripentadecanoin, tripalmitin, glyceryl triheptadecanoate, triolein, and so on.

The monooleoyl glycerol is also referred to as monoolein. A commercially available monooleoyl glycerol (e.g., Rylo MG 19™, Danisco) may be also used.

The surfactant includes polyoxyethylene-polyoxypropylene block copolymer (e.g., Poloxamer™), sorbitan ester (e.g., Span™), polyoxyethylene sorbitan (e.g., Tween™), polyoxyethylene ether (e.g., Brij™), and so on.

In an embodiment, the pharmaceutical composition of the present invention may comprise 4 to 25% by weight of the taxane, 10 to 20% by weight of the medium chain triglyceride, 40 to 60% by weight of monooleoyl glycerol, 10 to 25% by weight of the surfactant, and 10 to 20% by weight of polyoxyl glyceryl fatty acid ester. The pharmaceutical composition for oral administration is preferably in the form filled in a capsule such as a soft capsule.

In accordance with another aspect of the present invention, there is provided a process for preparing a pharmaceutical composition for oral administration, comprising (i) dissolving 4 to 40% by weight of a taxane and 10 to 30% by weight of polyoxyl glyceryl fatty acid ester in an organic solvent, (ii) removing the organic solvent from the solution obtained in Step (i), followed by mixing 10 to 30% by weight of a medium chain triglyceride, 30 to 70% by weight of monooleoyl glycerol, and 5 to 30% by weight of a surfactant therewith to form a solution, and (iii) optionally, filling the solution obtained in Step (ii) in a capsule.

In accordance with still another aspect of the present invention, there is provided a process for preparing a pharmaceutical composition for oral administration, comprising (i') dissolving 4 to 40% by weight of a taxane, 10 to 30% by weight of a medium chain triglyceride, 30 to 70% by weight of monooleoyl glycerol, 5 to 30% by weight of a surfactant, and 10 to 30% by weight of polyoxyl glyceryl fatty acid ester in an organic solvent, (ii') removing the organic solvent from the solution obtained in Step (i'), and (iii') optionally, filling the solution obtained in Step (ii') in a capsule.

In the processes of the present invention, said monooleoyl glycerol, taxane, medium chain triglyceride, surfactant, and polyoxyl glyceryl fatty acid ester are as described above.

In the processes of the present invention, the organic solvent may be one or more selected from the group consisting of a halogenated alkyl compound, an alcohol, and a ketone. The halogenated alkyl compound may be one or more selected from the group consisting of halogenated $C_1$ to $C_5$ alkyl compounds, preferably methylene chloride or chloroform, more preferably methylene chloride. The alcohol may be one or more selected from the group consisting of $C_1$ to $C_5$ lower alcohols, preferably methanol, ethanol or isopropyl alcohol, more preferably ethanol. The ketone may be acetone.

The organic solvent may be used in an amount capable of dissolving the taxane and the medium chain triglyceride, preferably in the amount of 0.4 times to 20 times based on the volume of the medium chain triglyceride, more preferably in the same volume as the volume of the medium chain triglyceride, but is not limited thereto. Said amounts of the organic solvent, which makes it possible to dissolve the taxane such as paclitaxel and docetaxel sufficiently, can reduce the waste originated from the use of excessive amounts of the solvent and the unnecessary effort for removing the organic solvent. In the processes of the present invention, the step for removing the organic solvent may be performed according to conventional drying methods, for example, by drying under reduced pressure at 15 to 50° C., preferably at room temperature. Through performing the steps for dissolving with an organic solvent and removing the organic solvent as described above, it is possible to homogeneously mix the respective components in the resulting composition.

The present invention will be described in further detail with reference to the following examples and experimental examples. These examples and experimental examples are for illustrative purposes only and are not intended to limit the scope of the present invention.

Example 1

Docetaxel-Containing Soft Capsules

The docetaxel-containing pharmaceutical composition for oral administration was prepared according to the components and amounts shown in Table 1. Docetaxel and LABRASOL™ (Gattefosse) were completely dissolved in ethanol (about 14 times of the volume of tricaprylin). The resulting solution was dried under reduced pressure at 40° C. to remove ethanol. To the resulting mixture, were added tricaprylin (Captex™ 8000, ABITEC), monooleoyl glycerol (Rylo MG 19™, Danisco), and Tween™ 80. The resulting mixture was stirred at 40° C. to obtain the clear oily solution. The resulting clear oily solution was filled into a soft capsule. The appearance of the clear oily solution is shown in FIG. 1 (left, A).

TABLE 1

| L/I | | Component | Amount/1 capsule | Ratio (% by weight) |
|---|---|---|---|---|
| 1 | Taxane | Docetaxel | 50 mg | 4.84 |
| 2 | Medium chain triglyceride | Tricaprylin | 0.14 ml | 12.77 |
| 3 | Monooleoyl glycerol | Rylo MG 19 ™ | 0.56 ml | 50.65 |
| 4 | Surfactant | Tween ™ 80 | 0.16 ml | 17.42 |
| 5 | Polyoxyl glyceryl fatty acid ester | LABRASOL ™ | 0.14 ml | 14.32 |
| | | Total | | 100.00 |

Example 2

The docetaxel-containing pharmaceutical composition for oral administration in the soft capsule form was prepared in accordance with the same procedures as in Example 1, using triacetin (Sigma) instead of tricaprylin.

Example 3

The docetaxel-containing pharmaceutical composition for oral administration in the soft capsule form was prepared in accordance with the same procedures as in Example 1, using tripropionin (Sigma) instead of tricaprylin.

Example 4

The docetaxel-containing pharmaceutical composition for oral administration in the soft capsule form was prepared in accordance with the same procedures as in Example 1, using tributyrin (Sigma) instead of tricaprylin.

Example 5

The docetaxel-containing pharmaceutical composition for oral administration in the soft capsule form was prepared in accordance with the same procedures as in Example 1, using trivalerin (Sigma) instead of tricaprylin.

Example 6

The docetaxel-containing pharmaceutical composition for oral administration in the soft capsule form was prepared in accordance with the same procedures as in Example 1, using tricaproin (Sigma) instead of tricaprylin.

Example 7

The docetaxel-containing pharmaceutical composition for oral administration in the soft capsule form was prepared in accordance with the same procedures as in Example 1, using triheptanoin (Sigma) instead of tricaprylin.

Example 8

The docetaxel-containing pharmaceutical composition for oral administration in the soft capsule form was prepared in accordance with the same procedures as in Example 1, using trinonanoin (Sigma) instead of tricaprylin.

Example 9

The docetaxel-containing pharmaceutical composition for oral administration in the soft capsule form was prepared in accordance with the same procedures as in Example 1, using tricaprin (Sigma) instead of tricaprylin.

Example 10

The docetaxel-containing pharmaceutical composition for oral administration in the soft capsule form was prepared in accordance with the same procedures as in Example 1, using triundecanoin (Sigma) instead of tricaprylin.

Example 11

The docetaxel-containing pharmaceutical composition for oral administration in the soft capsule form was prepared in accordance with the same procedures as in Example 1, using trilaurin (Sigma) instead of tricaprylin.

Example 12

The docetaxel-containing pharmaceutical composition for oral administration in the soft capsule form was prepared in accordance with the same procedures as in Example 1, using tritridecanoin (Sigma) instead of tricaprylin.

Example 13

The docetaxel-containing pharmaceutical composition for oral administration in the soft capsule form was prepared in accordance with the same procedures as in Example 1, using trimyristin (Sigma) instead of tricaprylin.

Example 14

The docetaxel-containing pharmaceutical composition for oral administration in the soft capsule form was prepared in accordance with the same procedures as in Example 1, using tripentadecanoin (Sigma) instead of tricaprylin.

Example 15

The docetaxel-containing pharmaceutical composition for oral administration in the soft capsule form was prepared in accordance with the same procedures as in Example 1, using tripalmitin (Sigma) instead of tricaprylin.

Example 16

The docetaxel-containing pharmaceutical composition for oral administration in the soft capsule form was prepared in accordance with the same procedures as in Example 1, using glyceryl triheptadecanoate (Sigma) instead of tricaprylin.

Example 17

The docetaxel-containing pharmaceutical composition for oral administration in the soft capsule form was prepared in accordance with the same procedures as in Example 1, using triolein (Sigma) instead of tricaprylin.

Example 18

The docetaxel-containing pharmaceutical composition for oral administration in the soft capsule form was prepared in accordance with the same procedures as in Example 1, using methylene chloride instead of anhydrous ethanol.

Example 19

The docetaxel-containing pharmaceutical composition for oral administration in the soft capsule form was prepared in accordance with the same procedures as in Example 1, using Gelucire™ 44/14 (Gettafosse) instead of LABRASOL™.

Example 20

The docetaxel-containing pharmaceutical composition for oral administration in the soft capsule form was prepared in accordance with the same procedures as in Example 1, using Gelucire™ 50/13 (Gettafosse) instead of LABRASOL™.

Example 21

Paclitaxel-Containing Soft Capsules

Figure 2:
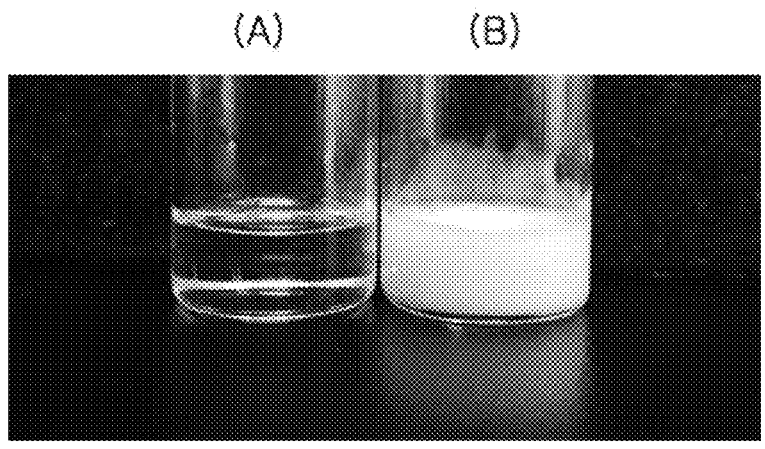
FIG. 2 represents the appearances of the paclitaxel-containing lipid solutions prepared in Example 21 and Comparative Example 2. A: the paclitaxel-containing lipid solution prepared in Example 21, B: the paclitaxel-containing lipid solution prepared in Comparative Example 2.

The paclitaxel-containing pharmaceutical composition for oral administration was prepared according to the components and amounts shown in Table 2. Paclitaxel and LABRASOL™ (Gattefosse) were completely dissolved in methylene chloride (about 14 times of the volume of tricaprylin). The resulting solution was dried under reduced pressure at 40° C. to remove methylene chloride. To the resulting mixture, were added tricaprylin (Captex™ 8000, ABITEC), monooleoyl glycerol (Rylo MG 19™, Danisco), and Tween™ 80. The resulting mixture was stirred at 40° C. to obtain the clear oily solution. The resulting clear oily solution was filled into a soft capsule. The appearance of the oily solution is shown in FIG. 2 (left, A).

TABLE 2

| L/I | | Component | Amount/1 capsule | Ratio (% by weight) |
|---|---|---|---|---|
| 1 | Taxane | Paclitaxel | 50 mg | 4.84 |
| 2 | Medium chain triglyceride | Captex ™ 8000 | 0.14 ml | 12.77 |
| 3 | Monooleoyl glycerol | Rylo MG 19 ™ | 0.56 ml | 50.65 |
| 4 | Surfactant | Tween ™ 80 | 0.16 ml | 17.42 |
| 5 | Polyoxyl glyceryl fatty acid ester | LABRASOL ™ | 0.14 ml | 14.32 |
| | | Total | | 100.00 |

Example 22

The paclitaxel-containing pharmaceutical composition for oral administration in the soft capsule form was prepared in accordance with the same procedures as in Example 21, using anhydrous ethanol instead of methylene chloride.

Example 23

The paclitaxel-containing pharmaceutical composition for oral administration in the soft capsule form was prepared in accordance with the same procedures as in Example 21, using triacetin (Sigma) instead of tricaprylin.

Example 24

The paclitaxel-containing pharmaceutical composition for oral administration in the soft capsule form was prepared in accordance with the same procedures as in Example 21, using tripropionin (Sigma) instead of tricaprylin.

Example 25

The paclitaxel-containing pharmaceutical composition for oral administration in the soft capsule form was prepared in accordance with the same procedures as in Example 21, using tributyrin (Sigma) instead of tricaprylin.

Example 26

The paclitaxel-containing pharmaceutical composition for oral administration in the soft capsule form was prepared in accordance with the same procedures as in Example 21, using trivalerin (Sigma) instead of tricaprylin.

Example 27

The paclitaxel-containing pharmaceutical composition for oral administration in the soft capsule form was prepared in accordance with the same procedures as in Example 21, using tricaproin (Sigma) instead of tricaprylin.

Example 28

The paclitaxel-containing pharmaceutical composition for oral administration in the soft capsule form was prepared in accordance with the same procedures as in Example 21, using triheptanoin (Sigma) instead of tricaprylin.

Example 29

The paclitaxel-containing pharmaceutical composition for oral administration in the soft capsule form was prepared in accordance with the same procedures as in Example 21, using trinonanoin (Sigma) instead of tricaprylin.

Example 30

The paclitaxel-containing pharmaceutical composition for oral administration in the soft capsule form was prepared in accordance with the same procedures as in Example 21, using tricaprin (Sigma) instead of tricaprylin.

Example 31

The paclitaxel-containing pharmaceutical composition for oral administration in the soft capsule form was prepared in accordance with the same procedures as in Example 21, using triundecanoin (Sigma) instead of tricaprylin.

Example 32

The paclitaxel-containing pharmaceutical composition for oral administration in the soft capsule form was prepared in accordance with the same procedures as in Example 21, using trilaurin (Sigma) instead of tricaprylin.

Example 33

The paclitaxel-containing pharmaceutical composition for oral administration in the soft capsule form was prepared in accordance with the same procedures as in Example 21, using tritridecanoin (Sigma) instead of tricaprylin.

Example 34

The paclitaxel-containing pharmaceutical composition for oral administration in the soft capsule form was prepared in accordance with the same procedures as in Example 21, using trimyristin (Sigma) instead of tricaprylin.

Example 35

The paclitaxel-containing pharmaceutical composition for oral administration in the soft capsule form was prepared in accordance with the same procedures as in Example 21, using tripentadecanoin (Sigma) instead of tricaprylin.

Example 36

The paclitaxel-containing pharmaceutical composition for oral administration in the soft capsule form was prepared in accordance with the same procedures as in Example 21, using tripalmitin (Sigma) instead of tricaprylin.

Example 37

The paclitaxel-containing pharmaceutical composition for oral administration in the soft capsule form was prepared in accordance with the same procedures as in Example 21, using glyceryl triheptadecanoate (Sigma) instead of tricaprylin.

Example 38

The paclitaxel-containing pharmaceutical composition for oral administration in the soft capsule form was prepared in accordance with the same procedures as in Example 21, using triolein (Sigma) instead of tricaprylin.

Example 39

The paclitaxel-containing pharmaceutical composition for oral administration in the soft capsule form was prepared in accordance with the same procedures as in Example 21, using Gelucire™ 44/14 (Gettafosse) instead of LABRASOL™.

Example 40

The paclitaxel-containing pharmaceutical composition for oral administration in the soft capsule form was prepared in accordance with the same procedures as in Example 21, using Gelucire™ 50/13 (Gettafosse) instead of LABRASOL™.

Example 41

Paclitaxel-Containing Soft Capsules

The paclitaxel-containing pharmaceutical composition for oral administration was prepared according to the components and amounts shown in Table 3. Paclitaxel and LABRASOL™ (Gattefosse) were completely dissolved in methylene chloride (about 14 times of the volume of tricaprylin). The resulting solution was dried under reduced to pressure at 40° C. to remove methylene chloride. To the resulting mixture, were added tricaprylin (Captex™ 8000, ABITEC), monooleoyl glycerol (Rylo MG 19™, Danisco), and Tween™ 80. The resulting mixture was stirred at 40° C. to obtain the clear oily solution. The resulting clear oily solution was filled into a soft capsule.

TABLE 3

| L/I | Component | | Amount/1 capsule | Ratio (% by weight) |
|---|---|---|---|---|
| 1 | Taxane | Paclitaxel | 250 mg | 20.55 |
| 2 | Medium chain triglyceride | Captex™ 8000 | 0.14 ml | 10.11 |
| 3 | Monooleoyl glycerol | Rylo MG 19™ | 0.56 ml | 43.72 |
| 4 | Surfactant | Tween™ 80 | 0.16 ml | 14.05 |
| 5 | Polyoxyl glyceryl fatty acid ester | LABRASOL™ | 0.14 ml | 11.57 |
| | Total | | | 100.00 |

Comparative Example 1

The docetaxel-containing composition was prepared according to the components and amounts shown in Table 4. Docetaxel and tricaprylin (Captex™ 8000, ABITEC) were completely dissolved in ethanol (about 14 times of the volume of tricaprylin). The resulting solution was dried under reduced pressure at 40° C. to remove ethanol. To the resulting mixture, were added monooleoyl glycerol (Rylo MG 19™, Danisco) and Tween™ 80. The resulting mixture was stirred at 40° C. to obtain the oily solution. The resulting oily solution was an opaque dispersion having white precipitates. The appearance thereof is shown in FIG. 1 (right, B).

TABLE 4

| L/I | Component | | Amount/1 capsule | Ratio (% by weight) |
|---|---|---|---|---|
| 1 | Taxane | Docetaxel | 30 mg | 3.01 |
| 2 | Medium chain triglyceride | Tricaprylin | 0.28 ml | 26.30 |
| 3 | Monooleoyl glycerol | Rylo MG 19™ | 0.56 ml | 52.49 |
| 4 | Surfactant | Tween™ 80 | 0.16 ml | 18.20 |
| | Total | | | 100.00 |

Comparative Example 2

The paclitaxel-containing composition was prepared according to the components and amounts shown in Table 5. Paclitaxel and tricaprylin (Captex™ 8000, ABITEC) were completely dissolved in methylene chloride (about 14 times of the volume of tricaprylin). The resulting solution was dried under reduced pressure at 40° C. to remove methylene chloride. To the resulting mixture, were added monooleoyl glycerol (Rylo MG 19™, Danisco) and Tween™ 80. The resulting mixture was stirred at 40° C. to obtain the oily solution. The resulting oily solution was an opaque dispersion having white precipitates. The appearance thereof is shown in FIG. 2 (right, B).

TABLE 5

| L/I | Component | Amount/1 capsule | Ratio (% by weight) |
|---|---|---|---|
| 1 | Taxane | Paclitaxel | 30 mg | 3.01 |
| 2 | Medium chain triglyceride | Tricaprylin | 0.28 ml | 26.30 |
| 3 | Monooleoyl glycerol | Rylo MG 19 ™ | 0.56 ml | 52.49 |
| 4 | Surfactant | Tween ™ 80 | 0.16 ml | 18.20 |
| | | Total | | 100.00 |

Experimental Example 1

Stability Evaluation of Gelatin Capsules

The soft capsules prepared in Example 1 and Example 21 were placed in a HDPE bottle, which were then stored under the conditions of 25° C. and 60% (RH) for 6 months to evaluate the stability of the gelatin capsules. Stability of the gelatin capsules was evaluated through observing the appearances thereof and a leak therefrom. The results are shown in the following Table 6.

TABLE 6

| | | Example 1 | Example 21 |
|---|---|---|---|
| 1 month | Leak | No leak occurred | No leak occurred |
| | Appearance | No appearance changed | No appearance changed |
| 3 months | Leak | No leak occurred | No leak occurred |
| | Appearance | No appearance changed | No appearance changed |
| 6 months | Leak | No leak occurred | No leak occurred |
| | Appearance | No appearance changed | No appearance changed |

From the results of Table 6, it can be seen that the soft capsules prepared according to the present invention have excellent stability.

The invention claimed is:

1. A soft capsule filled with a clear solution consisting of:
   (a) 4 to 40% by weight of paclitaxel or docetaxel,
   (b) 10 to 30% by weight of a medium chain triglyceride selected from the group consisting of triacetin, tripropionin, tributyrin, trivalerin, tricaproin, tricaprylin, tricaprin, triheptanoin, trinonanoin, triundecanoin, trilaurin, tritridecanoin, trimyristin, tripentadecanoin, tripalmitin, glyceryl triheptadecanoate, and triolein,
   (c) 30 to 70% by weight of monooleoyl glycerol,
   (d) 5 to 30% by weight of polyoxyethylene (80) sorbitan monooleate as a surfactant, and
   (e) 10 to 30% by weight of polyoxyl glyceryl fatty acid ester selected from the group consisting of caprylocaproyl polyoxyl glyceride, lauroyl polyoxyl glyceride, and stearoyl polyoxyl glyceride.

2. The soft capsule according to claim 1, wherein the polyoxyl glyceryl fatty acid ester is one or more selected from the group consisting of caprylocaproyl polyoxyl-32 glyceride, lauroyl polyoxyl-32 glyceride, and stearoyl polyoxyl-32 glyceride.

3. The soft capsule according to claim 1, consisting of 4 to 25% by weight of paclitaxel or docetaxel, 10 to 20% by weight of the medium chain triglyceride, 40 to 60% by weight of monooleoyl glycerol, 10 to 25% by weight of polyoxyethylene (80) sorbitan monooleate, and 10 to 20% by weight of the polyoxyl glyceryl fatty acid ester.

* * * * *